(12) United States Patent
Hunt

(10) Patent No.: US 6,383,173 B1
(45) Date of Patent: May 7, 2002

(54) SYRINGE DRENCH ADAPTER FOR LIVESTOCK

(76) Inventor: Roy H. Hunt, P.O. Box 2087, Rosamond, CA (US) 93560

( * ) Notice: Subject to any disclaimer, the term of this patent is extended or adjusted under 35 U.S.C. 154(b) by 0 days.

(21) Appl. No.: 09/426,121

(22) Filed: Oct. 22, 1999

(51) Int. Cl.[7] .............................................. A61M 5/00
(52) U.S. Cl. ....................... 604/533; 604/187; 604/240; 604/257
(58) Field of Search ................................ 604/533, 181, 604/187, 240, 257, 261, 275, 523

(56) References Cited

U.S. PATENT DOCUMENTS

| | | | | |
|---|---|---|---|---|
| 4,123,091 A | * | 10/1978 | Cosentino et al. ............. 285/39 |
| 4,200,096 A | * | 4/1980 | Charvin ....................... 604/164 |
| 4,323,071 A | * | 4/1982 | Simpson et al. ............ 128/343 |
| 4,343,306 A | * | 8/1982 | Mericle ....................... 604/218 |
| 4,384,581 A | * | 5/1983 | Conway ....................... 604/207 |
| 4,405,322 A | * | 9/1983 | Jessup ......................... 604/232 |
| 4,411,055 A | * | 10/1983 | Simpson et al. .............. 29/447 |
| 4,736,732 A | * | 4/1988 | Shimonaka et al. ........ 600/158 |
| 4,828,547 A | * | 5/1989 | Sahi et al. ................... 604/110 |
| 4,909,791 A | * | 3/1990 | Norelli ....................... 604/192 |
| 5,002,538 A | * | 3/1991 | Johnson ....................... 604/240 |
| 5,112,327 A | * | 5/1992 | Iinuma et al. ............... 604/413 |
| 5,851,201 A | * | 12/1998 | Ritger et al. ................ 604/240 |
| 5,919,169 A | * | 7/1999 | Grams et al. | |

* cited by examiner

*Primary Examiner*—Brian L. Casler
*Assistant Examiner*—Kevin C. Sirmons
(74) *Attorney, Agent, or Firm*—Kelly Bauersfeld Lowry & Kelley, LLP

(57) ABSTRACT

A syringe drench adapter for livestock includes a collar having a frustroconical nose and a generally cylindrical skirt extending from the nose which is removably fittable over an end of a syringe, and an elongated tube extending from the nose. The skirt defines a syringe-receiving opening having an inner diameter which is less than an outer diameter of the syringe barrel. The skirt includes a circumferential ridge which extends radially inwardly and is disposed adjacent to the syringe-receiving opening, and a plurality of longitudinal slots extending from the syringe-receiving opening which provide flexion. The slots are disposed about the periphery of the skirt and are configured so as to reveal syringe measurement markings when the collar is fitted over the end of the syringe. The elongated tube defines a fluid passageway having an inlet removably connected to the nose of the collar, and an outlet for the expulsion of fluids. The fluid passageway adjacent to the inlet is configured to form-fit a nozzle of the syringe.

27 Claims, 2 Drawing Sheets

US 6,383,173 B1

SYRINGE DRENCH ADAPTER FOR LIVESTOCK

BACKGROUND OF THE INVENTION

The present invention relates to livestock drenches. More particularly, the present invention relates to a livestock drench adapter for use with a traditional syringe.

Veterinarians and livestock owners oftentimes must orally administer fluids, such as liquid medications, to livestock and other animals. This procedure is oftentimes referred to as drenching. Particularly in the case of liquid medications, the dosage may be relatively low and the liquid may be highly concentrated. Due to the need for proper dosage as well as the expense of the medication, it is desirable to accurately and fully administer the drench solution.

A variety of drenching guns are currently used to deliver drench to the mouth of the animal, such as a cow, sheep or horse. Drenching guns typically comprise a handle and cylinder adapted to deliver a quantity of drench solution to an elongated rod at the end of the device. The elongated rod is inserted into the animal's mouth. The cylinder usually includes measurement markings so that a measured dose may be given. The elongated rod has one end attached to an outlet end of the cylinder and also a discharge end opposite the cylinder. The elongated rod may be bent at a desired angle to facilitate administration of the drench solution to the animal. A piston within the cylinder is connected to a piston rod which is in turn connected to operating means to control the dosage. A trigger within the handle may be employed as part of the operating means to administer the dosage, and may be configured to incrementally eject a predetermined amount of fluid so that several animals may be drenched before refilling the cylinder. Depending on the drench gun, the rate of flow of the drench solution may be adjusted and one-way valves may be used to prevent backflow into the cylinder.

Although currently used drench guns perform adequately, many livestock owners do not own a drench gun due to cost and storage limitations. Instead, these livestock owners use syringes to drench the animal. Syringes are relatively inexpensive and are used for a variety of other procedures, such as intradermal injections, so it is common for the veterinarian or livestock owner to readily have syringes on hand. However, there are problems associated with using standard syringes. The syringe is usually composed of a plastic which is easily damaged when forced into the mouth of the animal. It is also not uncommon for the animal to chew on the end of the syringe during drenching, rendering the syringe incapable of future use. Another problem experienced when using syringes to drench animals is that syringes have relatively short nozzles. Therefore, in order that the drench solution not be lost, a portion of the syringe itself must be inserted into the animal's mouth. This also prohibits the viewing of the measurement markings on the syringe during drenching. Insertion of the syringe into the animal's mouth further requires that the undamaged syringe be cleaned before its next use so as not to contaminate the drench solution.

Accordingly, there is a need for an adapter which provides the benefits of a drench gun while allowing use of traditional syringes. There is also a need for an adapter which is easily stored and transported, economical to manufacture and durable in use. The present invention fulfills these needs and provides other related advantages.

SUMMARY OF THE INVENTION

The present invention resides in a syringe drench adapter for livestock which adapts a traditional catheter syringe for use as a drench syringe. The syringe drench adapter of the present invention is economical, easily stored and transported. The syringe drench adapter is also efficient in operation and durable in use.

The present invention is intended to be used with syringes having a barrel, a plunger slidable within the barrel for the intake and expulsion of fluids, a cap formed on the barrel opposite the plunger and an open-ended nozzle extending from the cap.

The syringe drench adapter of the present invention includes a collar removably fittable over the cap and an adjacent portion of the barrel at an end of the syringe. The collar comprises a frustroconical nose and a generally cylindrical skirt extending from the nose. The skirt defines a syringe-receiving opening having an inner diameter which is less than an outer diameter of the syringe barrel so as to form a tight friction fit between the skirt and the syringe. The skirt includes a plurality of longitudinal slots extending from the syringe-receiving opening which provide flexion, and a circumferential ridge which extends radially inwardly and is disposed adjacent to the syringe-receiving opening. The slots are disposed about the periphery of the skirt and are configured so as to reveal syringe measurement markings when the collar is fitted over the end of the syringe.

An elongated tube extends from the nose of the collar and defines a fluid passageway having an inlet removably connected to the nose of the collar and an outlet opposite the inlet for the expulsion of fluids. The nose includes an interiorly threaded aperture for threadably receiving a portion of the elongated tube defining the inlet. The fluid passageway adjacent to the inlet is configured to form-fit the nozzle of the syringe. In one form, the elongated tube includes abutting inlet and outlet sections which are angularly offset from one another to form a bend in the elongated tube.

The collar and elongated tube of the syringe drench adapter are preferably comprised of metal so as to be durable, washable and reusable.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 5:
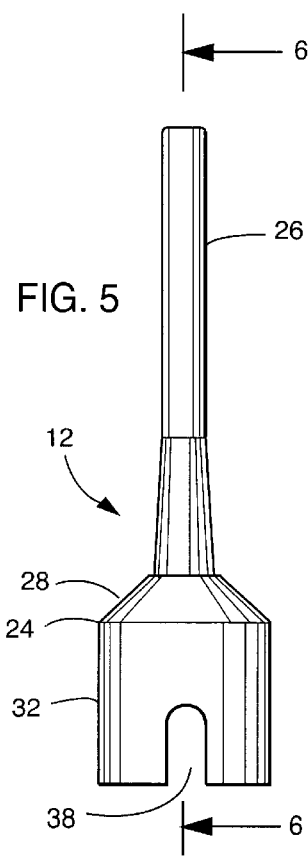
FIG. 5 is an elevational view of a second embodiment of the syringe drench adapter of the present invention.
Figure 6:
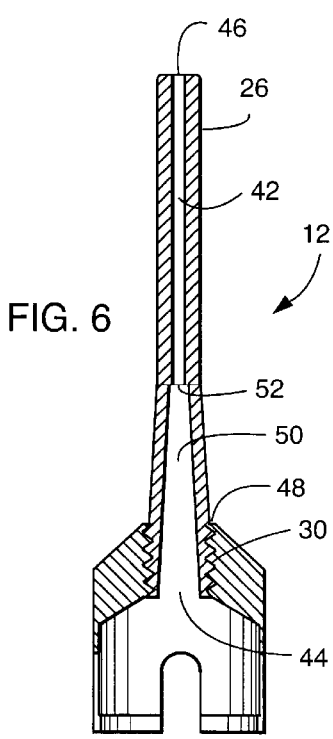
FIG. 6 is a cross-sectional view of the drench adapter of FIG. 5 taken along line 6—6 thereof, illustrating the threaded connection between the elongated tube and collar and the taper of the elongated tube which form-fits a nozzle of a syringe.

As shown in the drawings for purposes of illustration, the present invention is concerned with a syringe drench adapter, generally referred to by the reference number 10 in FIGS. 1–4, and by the reference number 12 in FIGS. 5 and 6. The drench adapters 10 and 12 are used with a syringe 14, such as a catheter syringe.

Figure 1:
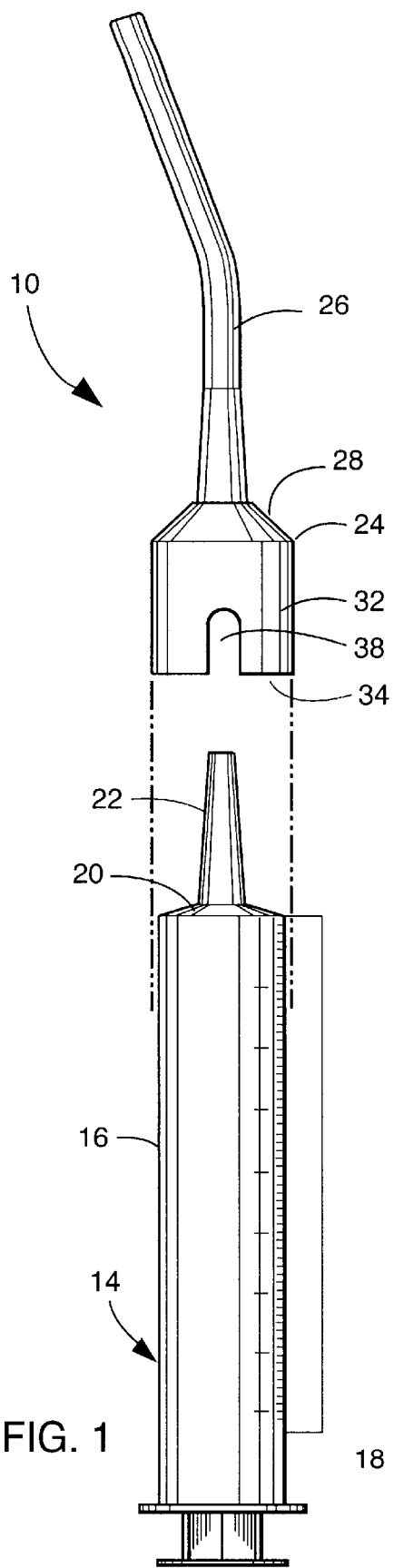
FIG. 1 is an exploded side elevational view of a drench adapter embodying the present invention.
Figure 2:
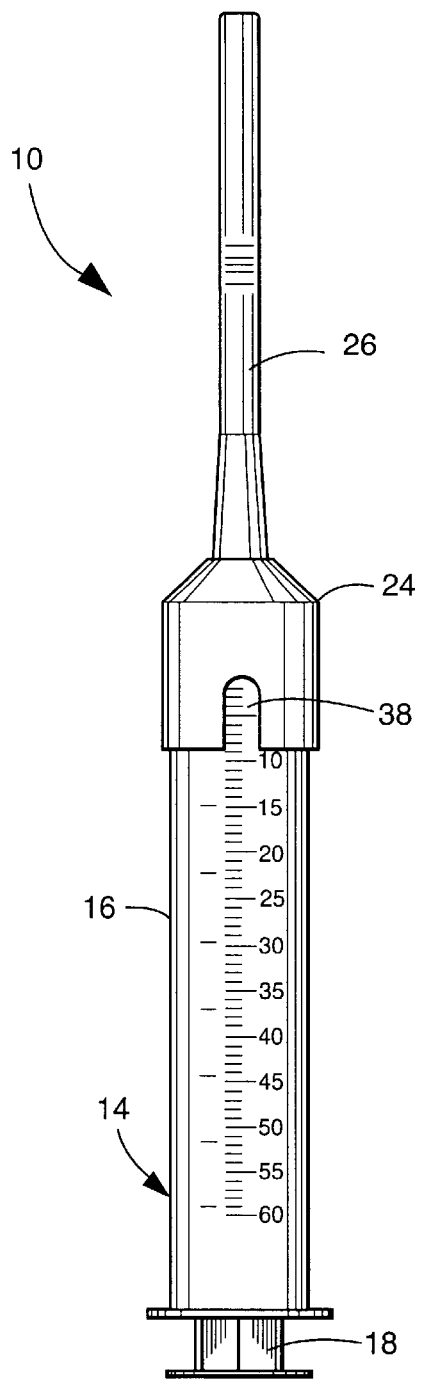
FIG. 2 is a front elevational assembled view of the drench adapter and syringe of FIG. 1, illustrating the alignment of a slot with measurement markings on the syringe.

A typical catheter syringe 14, as illustrated in FIGS. 1 and 2, generally comprises a cylindrical barrel 16 which holds a liquid. A plunger and rod 18 are inserted into an open end of the barrel 16 and are sized so as to be movable in and out of the barrel to either draw liquid into the barrel or expel the liquid out of the barrel while maintaining a liquid-tight seal with the barrel 16. On an end of the barrel 16 opposite the plunger and rod 18 is formed a cap 20 and a hollow open-ended nozzle 22 which extends outwardly from the cap 20. The cap 20 is typically somewhat conical in shape to facilitate fluid flow into and out of the syringe 14. The nozzle 22 extends from the cap 20 only a fraction of an inch to perhaps two inches depending on the size and design of the syringe 14. The nozzle 22 may be generally cylindrical, or may also be tapered as illustrated in FIG. 1.

The drench adapters 10 and 12 are removably fitted over the cap 20 and an adjacent portion of the barrel 16 of the syringe 14. The drench adapters 10 and 12 are each generally comprised of a collar 24 and an elongated tube 26. The collar 24 includes a frustroconical nose 28 having an angled interior surface which generally matches the conical surface of the cap 20. An aperture 30 is formed in the nose 28 and is interiorly threaded to receive the elongated tube 26.

Figure 3:
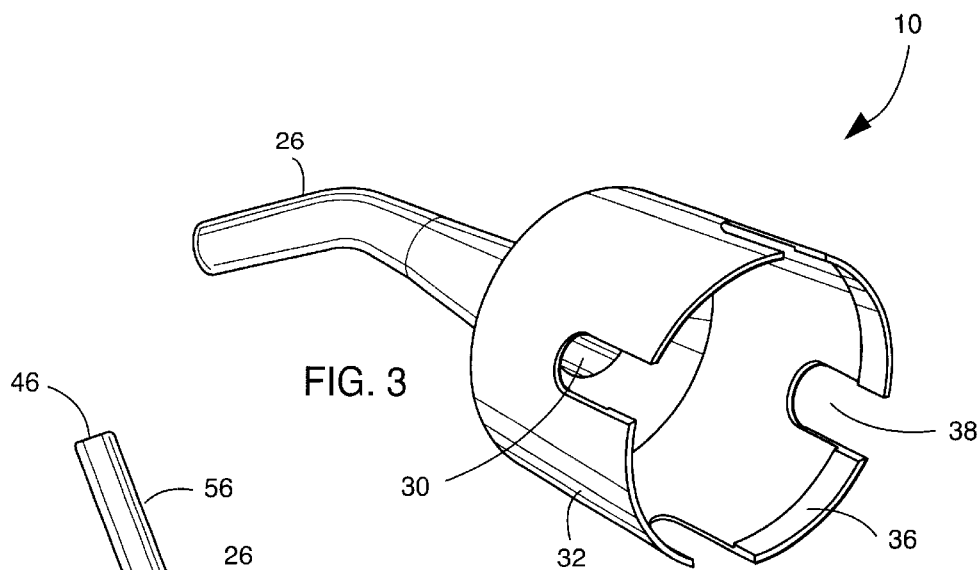
FIG. 3 is a perspective view of the drench adapter of FIGS. 1 and 2.
Figure 4:
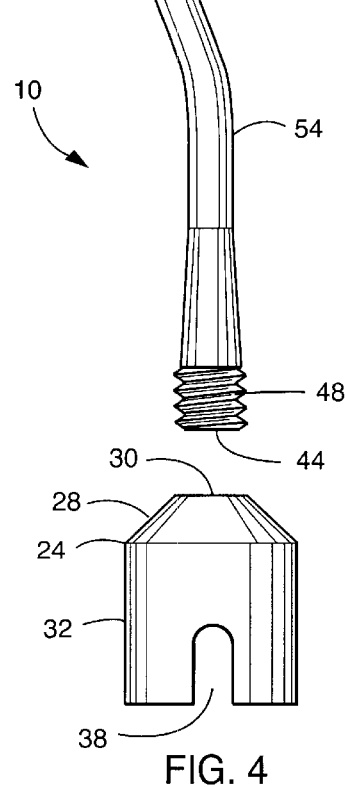
FIG. 4 is an elevational view of an elongated tube separated from a collar of the syringe drench adapter of FIGS. 1–3.

A cylindrical skirt 32 extends from the nose 28 to define a syringe-receiving opening 34. A ridge 36 extends radially inwardly about the circumference of the skirt 32 adjacent the syringe-receiving opening 34, as illustrated in FIG. 3. The inner diameter of the skirt 32 at the ridge 36 is less than the outer diameter of the barrel 16 of the syringe 14 so that a tight frictional fit is formed when the collar 24 is placed over the syringe 14. The nominal inner diameter of the skirt 32, however, is typically slightly greater than the outer diameter of the barrel 16 of the syringe 14. Longitudinal slots 38 are formed in the skirt 32 to provide flexion and expansion of the skirt 32 to allow the placement and removal of the collar 24 to the syringe 14. The slots 38 are sized and configured so as to, when properly aligned, allow reading of measurement markings 40 of the syringe 14 even when the collar 20 is placed over the end of the syringe 14.

The elongated tube 26 forms a fluid passageway 42 having an inlet 44 and an outlet 46 opposite the inlet 44. The elongated tube 26 extends from the nose 28 of the collar 24. Typically, an exterior portion of the tube adjacent the inlet 44 is threaded 48 so as to be removably screwed into the nose 28 of the collar 24. A portion 50 of the fluid passageway 42 adjacent to the inlet 44 is tapered to match and accept the taper of the inserted nozzle 22. The tapered portion 50 acts to form a tight seal with the inserted nozzle 22 which prevents movement of the nozzle 22 within the elongated tube 26. Thus, when the drench adapter 10 or 12 is properly fitted to the syringe 14, the points of engagement between the two are at the ridge 36 and the tapered portion 50. Other facing components of the syringe 14 and the drench adapter 10 or 12 are slightly spaced from one another.

The elongated tube 26 may include abutting inlet and outlet sections 54 and 56 which are angularly offset from one another, resulting in a bend in the elongated tube 26 of the adapter 10, as illustrated in FIGS. 1–4. The inlet and outlet sections 54 and 56 are preferably formed integrally with one another. It is believed that such a bend in the elongated tube 26 facilitates the insertion of the elongated tube 26 into the mouth or even throat of certain animals. The elongated tube 26 may also be continuously linear, as illustrated in FIGS. 5 and 6.

In use, the drench is drawn into the syringe 14. This may be done with or without the drench adapter 10 and 12 fitted onto the syringe 14. Assuming the drench is drawn without the adapter 10 or 12, prior to dispensing the drench the elongated tube 26 is screwed into the nose aperture 30 and the collar 24 is forcibly inserted over the cap 20, nozzle 22 and adjoining portion of the barrel 16. The elongated tube 26 is forced into the animal's mouth and the proper dosage of drench is administered. As with drench guns, several animals may be drenched with a single syringe 14 full of liquid drench as the administer can view the syringe measurement markings 40.

The syringe drench adapters 10 and 12 are comprised of any suitable durable material, but metal is preferred. After drenching, the drench adapter 10 or 12 may be removed from the syringe 14 and washed. It should be noted that the nozzle 22 fits so tightly within the tapered portion 50 that removal of the drench adapter 10 and 12 may not be necessary to clean the adapter 10 and 12 and the syringe 14. The elongated tube 26 may be further removed for cleaning or compact storage. The typically plastic syringe 14 is protected during the drenching by the metal drench adapter 10 and 12, and may thus be used for later drenchings, or intradermal injections.

Although several embodiments have been described in detail for purposes of illustration, various modifications may be made without departing from the scope and spirit of the invention. Accordingly, the invention is not to be limited, except as by the appended claims.

What is claimed is:

1. A syringe drench adapter for livestock, comprising:

a collar removably fittable over an end of a syringe, the collar including a frustroconical nose configured to be placed over a nozzle of the syringe and a generally cylindrical skirt extending from the nose, the skirt defining a syringe barrel-receiving opening having an inner diameter which is substantially equal to or less than an outer diameter of a barrel of the syringe, the skirt including a plurality of longitudinal slots extending from the syringe barrel-receiving opening to facilitate a removable frictional fit with the syringe barrel; and an elongated tube extending from the nose of the collar, and defining a fluid passageway for the expulsion of fluids through an outlet at an end of the tube opposite the nose of the collar, wherein a portion of the elongated tube defining an inlet thereof is removably connected to the nose of the collar, the inlet being tapered and thereby configured to form-fit the nozzle of the syringe, and wherein the nose includes an interiorly threaded aperture for threadably receiving the portion of the elongated tube defining the inlet.

2. The adapter of claim 1, wherein the elongated tube includes inlet and outlet sections which are angularly offset from one another.

3. The adapter of claim 1, wherein the slots are disposed about the periphery of the skirt and are configured so as to reveal syringe measurement markings when the collar is fitted over an end of the syringe.

4. The adapter of claim 1, wherein the skirt includes a circumferential ridge which extends radially inwardly and is disposed adjacent to the syringe-receiving opening.

5. The adapter of claim 1, wherein the skirt includes a circumferential ridge which extends radially inwardly and is disposed adjacent to the syringe barrel-receiving opening.

6. A syringe drench adapter for livestock, comprising:

a collar removably fittable over an end of a syringe, the collar including a frustroconical nose configured to be placed over a nozzle of the syringe and a generally cylindrical skirt extending from the nose, the skirt defining a syringe barrel-receiving opening having an inner diameter which is substantially equal to or less than an outer diameter of a barrel of the syringe, the skirt including a plurality of longitudinal slots extending from the syringe barrel-receiving opening and a circumferential ridge which extends radially inwardly and is disposed adjacent to the syringe barrel-receiving opening to facilitate a removable frictional fit with the syringe barrel; and an elongated tube removably connected to the nose of the collar defining a fluid passageway, and having an inlet configured to form-fit a nozzle of the syringe, and an outlet at an end of the tube opposite the inlet for the expulsion of fluids.

7. The adapter of claim 6, wherein the elongated tube includes inlet and outlet sections which are angularly offset from one another.

8. The adapter of claim 6, wherein the slots are disposed about the periphery of the skirt and are configured so as to reveal syringe measurement markings when the collar is fitted over an end of the syringe.

9. The adapter of claim 6, wherein the collar and elongated tube are formed of metal.

10. A combination drench adapter and syringe for livestock, comprising:

a syringe having a barrel, a plunger slidable within the barrel, a cap formed on the barrel opposite the plunger, and a nozzle extending from the cap; and a drench adapter comprising:

a collar removably fittable over the cap and an adjacent portion of the barrel of the syringe, the collar including a frustroconical nose and a generally cylindrical skirt extending from the nose, the skirt defining a syringe-receiving opening having an inner diameter which is substantially equal to or less than an outer diameter of the barrel of the syringe, the skirt including a plurality of longitudinal slots extending from the syringe-receiving opening and, a circumferential ridge which extends radially inwardly and is disposed adjacent to the syringe-receiving opening; and an elongated tube removably connected to the nose of the collar defining a fluid passageway, and having an outlet at an end of the tube opposite an inlet thereof for the expulsion of fluids;

wherein the nose includes an interiorly threaded aperture for threadably receiving the portion of the elongated tube defining the inlet.

11. The combination of claim 10, wherein the inlet is tapered and thereby configured to form-fit a nozzle of the syringe.

12. The combination of claim 11, wherein the drench adapter and the syringe engage one another only at the circumferential ridge and the fluid passageway adjacent to the inlet of the elongated tube.

13. The combination of claim 10, wherein the elongated tube includes inlet and outlet sections which are angularly offset from one another.

14. The combination of claim 10, wherein the slots are disposed about the periphery of the skirt and are configured so as to reveal syringe measurement markings.

15. The combination of claim 10, wherein the collar and the elongated tube are formed of metal.

16. The adapter of claim 1, wherein the collar and elongated tube are formed of metal.

17. A syringe drench adapter for livestock, comprising:

a collar removably fittable over an end of a syringe, the collar including a frustroconical nose configured to be placed over a nozzle of the syringe and a generally cylindrical skirt extending from the nose, the skirt defining a syringe barrel-receiving opening having an inner diameter which is substantially equal to or less than an outer diameter of a barrel of the syringe, the skirt including a plurality of longitudinal slots extending from the syringe barrel-receiving opening to facilitate a removable frictional fit with the syringe barrel; and an elongated tube having an inlet extending from the nose of the collar, and defining a fluid passageway for the expulsion of fluids through an outlet at an end of the tube opposite the nose of the collar, wherein a portion of the elongated tube defining an inlet thereof is removably connected to the nose of the collar.

18. The adapter of claim 17, wherein the nose includes an interiorly threaded aperture for threadably receiving the portion of the elongated tube defining the inlet.

19. The adapter of claim 17, wherein the fluid passageway adjacent to the inlet is configured to form-fit a nozzle of the syringe.

20. The adapter of claim 17, wherein the slots are disposed about the periphery of the skirt and are configured so as to reveal syringe barrel measurement markings when the collar is fitted over an end of the syringe.

21. The adapter of claim 17, wherein the inlet and outlet sections of the elongated tube are angularly offset from one another.

22. A syringe drench adapter for livestock, comprising:

a collar removably fittable over an end of a syringe, the collar including a frustroconical nose configured to be placed over a nozzle of the syringe and a generally cylindrical skirt extending from the nose, the skirt defining a syringe barrel-receiving opening having an inner diameter which is substantially equal to or less than an outer diameter of a barrel of the syringe, the skirt including a plurality of longitudinal slots extending from the syringe barrel-receiving opening and a circumferential ridge which extends radially inwardly and is disposed adjacent to the syringe barrel-receiving opening; and an elongated tube extending from the nose of the collar, and defining a fluid passageway for the expulsion of fluids through an outlet at an end of the tube opposite the nose of the collar wherein the elongated tube includes an inlet section that is tapered and thereby configured to form-fit a nozzle of the syringe;

wherein the slots are disposed about the periphery of the skirt and are configured so as to reveal syringe barrel measurement markings when the collar is fitted over an end of the syringe; and wherein the nose includes an interiorly threaded aperture for threadably receiving the portion of the elongated tube defining the inlet.

23. The adapter of claim 22, wherein the inlet is tapered and thereby configured to form-fit a nozzle of the syringe.

24. The adapter of claim 22, wherein the elongated tube includes inlet and outlet sections which are angularly offset from one another.

25. A syringe drench adapter for livestock, comprising:

a collar removably fittable over an end of a syringe, the collar including a frustroconical nose configured to be placed over a nozzle of the syringe and a generally cylindrical skirt extending from the nose, the skirt defining a syringe-receiving opening having an inner diameter which is substantially equal to or less than an outer diameter of the syringe, the skirt including a plurality of longitudinal slots extending from the syringe-receiving opening and a circumferential ridge which extends radially inwardly and is disposed adjacent to the syringe-receiving opening to facilitate a removable frictional fit with the syringe barrel; and an elongated tube extending from the nose of the collar and defining a fluid passageway having an outlet at an end of the tube opposite an inlet for the expulsion of fluids, wherein the inlet is tapered and thereby configured to form-fit the nozzle of the syringe;

wherein the nose includes an interiorly threaded aperture for threadably receiving the portion of the elongated tube defining the inlet.

26. The adapter of claim 25, wherein the elongated tube includes inlet and outlet sections which are angularly offset from one another.

27. The adapter of claim 25, wherein the slots are disposed about the periphery of the skirt and are configured so as to reveal syringe measurement markings when the collar is fitted over an end of the syringe.

* * * * *